(12) United States Patent
Van Liere (10) Patent No.: US 11,096,676 B2
(45) Date of Patent: Aug. 24, 2021

(54) BIOPSY DEVICE HAVING A HYDRAULIC DRIVE ASSEMBLY

(71) Applicant: C. R. Bard, Inc., Franklin Lakes, NJ (US)

(72) Inventor: Chad Van Liere, Phoenix, AZ (US)

(73) Assignee: C.R. Bard, Inc., Franklin Lakes, NJ (US)

( * ) Notice: Subject to any disclaimer, the term of this patent is extended or adjusted under 35 U.S.C. 154(b) by 315 days.

(21) Appl. No.: 16/344,211

(22) PCT Filed: Oct. 17, 2017

(86) PCT No.: PCT/US2017/056918
§ 371 (c)(1),
(2) Date: Apr. 23, 2019

(87) PCT Pub. No.: WO2018/093509
PCT Pub. Date: May 24, 2018

(65) Prior Publication Data
US 2019/0261963 A1  Aug. 29, 2019

Related U.S. Application Data

(60) Provisional application No. 62/424,913, filed on Nov. 21, 2016.

(51) Int. Cl.
*A61B 10/02* (2006.01)
*A61B 17/00* (2006.01)

(52) U.S. Cl.
CPC .. *A61B 10/0233* (2013.01); *A61B 2010/0208* (2013.01); *A61B 2017/00539* (2013.01)

(58) Field of Classification Search
CPC ........ A61B 10/0233; A61B 2010/0208; A61B 2017/00539
See application file for complete search history.

(56) References Cited

U.S. PATENT DOCUMENTS

| 4,605,011 A | 8/1986 | Naslund |
| 5,431,645 A | 7/1995 | Smith et al. |
| 5,626,607 A | 5/1997 | Malecki et al. |

(Continued)

FOREIGN PATENT DOCUMENTS

| WO | 2004028585 A2 | 4/2004 |
| WO | 2008024684 A2 | 2/2008 |

*Primary Examiner* — Sean P Dougherty
(74) *Attorney, Agent, or Firm* — Dinsmore & Shohl LLP (57) ABSTRACT

A biopsy device includes a hydraulic drive assembly, a drive mechanism, and a biopsy member. The hydraulic drive assembly includes a chamber housing that defines a proximal chamber, a distal chamber, and a transition chamber that collectively form a continuous passage in the chamber housing. The proximal chamber has a first transverse area and the distal chamber has a second transverse area, with the first transverse area being larger than the second transverse area. A drive piston is located in the proximal chamber and a driven piston is located in the distal chamber. A hydraulic fluid fills a cavity between the drive piston and the driven piston to establish a hydraulic connection between the drive piston and the driven piston. The drive mechanism is connected to the drive piston to move the drive piston in the proximal cylinder. The biopsy member is connected to the driven piston.

21 Claims, 6 Drawing Sheets

(56) References Cited

U.S. PATENT DOCUMENTS

| | | |
|---|---|---|
| 6,190,330 B1 | 2/2001 | Harhen |
| 6,485,436 B1 | 11/2002 | Truckai et al. |
| 6,551,255 B2 | 4/2003 | Van Bladel et al. |
| 6,758,824 B1 | 7/2004 | Miller et al. |
| 6,858,014 B2 | 2/2005 | Damarati |
| 7,008,383 B1 | 3/2006 | Damadian et al. |
| 7,311,672 B2 | 12/2007 | Van Bladel et al. |
| 7,497,833 B2 | 3/2009 | Miller |
| 7,618,413 B2 | 11/2009 | Weitzner et al. |
| 7,837,630 B2 | 11/2010 | Nicoson et al. |
| 7,963,928 B2 | 6/2011 | Krause |
| 8,038,627 B2 | 10/2011 | Hibner |
| 8,167,818 B2 | 5/2012 | Miller |
| 8,231,545 B2 | 7/2012 | Spero et al. |
| 8,277,393 B2 | 10/2012 | Miller et al. |
| 8,287,465 B2 | 10/2012 | Hardin et al. |
| 8,568,332 B2 | 10/2013 | Miller |
| 8,622,926 B2 | 1/2014 | Hibner |
| 8,721,563 B2 | 5/2014 | Taylor et al. |
| 8,986,222 B2 | 3/2015 | Miller et al. |
| 9,204,866 B2 | 12/2015 | Shabaz et al. |
| 2002/0055689 A1* | 5/2002 | Kaplan ............. A61B 10/0233 600/567 |
| 2002/0082519 A1 | 6/2002 | Miller et al. |
| 2003/0114838 A1 | 6/2003 | O'Neill et al. |
| 2005/0027210 A1* | 2/2005 | Miller ............... A61B 10/0275 600/567 |
| 2005/0065453 A1* | 3/2005 | Shabaz ............. A61B 10/0233 600/564 |
| 2006/0149163 A1* | 7/2006 | Hibner ............. A61B 10/0266 600/566 |
| 2007/0125826 A1* | 6/2007 | Shelton, IV ...... A61B 17/07207 227/175.1 |
| 2007/0219565 A1 | 9/2007 | Saadat |
| 2009/0018468 A1* | 1/2009 | Janssens ........... A61B 10/0266 600/567 |
| 2010/0030104 A1* | 2/2010 | Hardin ............. A61B 10/0275 600/566 |
| 2011/0071431 A1* | 3/2011 | Speeg ............... A61B 10/0275 600/567 |
| 2011/0124961 A1 | 5/2011 | Zimmon |
| 2011/0301604 A1* | 12/2011 | Horner ............. A61B 18/1445 606/52 |

\* cited by examiner

BIOPSY DEVICE HAVING A HYDRAULIC DRIVE ASSEMBLY

CROSS-REFERENCE TO RELATED APPLICATIONS

This application is a U.S. national phase of International Application No. PCT/US2017/056918, filed Oct. 17, 2017, which claims priority to U.S. provisional patent application Ser. No. 62/424,913 filed Nov. 21, 2016, each of which is incorporated herein by reference.

TECHNICAL FIELD

The present invention relates to biopsy devices for sampling tissue, and, more particularly, to a biopsy device having a hydraulic drive assembly.

BACKGROUND ART

A biopsy may be performed on a patient to help in determining whether the cells in a biopsied region are cancerous. One type of biopsy device for performing a biopsy includes a hand-held driver assembly having an electromechanical driver that is attachable to a disposable biopsy probe assembly. The biopsy device typically includes spring-loaded components that, when moved, intermittently contact other components, resulting in significant noise.

What is needed in the art is a biopsy device having a hydraulic drive assembly that operates in conjunction with electromechanical components to reduce or eliminate intermittent contact between movable components, thereby providing a noise reduction of the biopsy device.

SUMMARY OF INVENTION

The present invention provides a biopsy device having a hydraulic drive assembly that operates in conjunction with electromechanical components to reduce or eliminate intermittent contact between movable components, thereby providing a noise reduction of the biopsy device.

The invention in one form is directed to a biopsy device that includes a hydraulic drive assembly, a drive mechanism, and an elongate biopsy member. The hydraulic drive assembly includes a chamber housing configured to define a proximal chamber, a distal chamber, and a transition chamber. The transition chamber is interposed between the proximal chamber and the distal chamber, wherein the proximal chamber, the transition chamber, and the distal chamber collectively form a continuous passage in the chamber housing. The proximal chamber has a first transverse area and the distal chamber has a second transverse area, with the first transverse area being larger than the second transverse area. A drive piston is located in the proximal chamber and is configured to move in the proximal chamber. A driven piston is located in the distal chamber and is configured to move in the distal chamber. A cavity is defined in the chamber housing between the drive piston and the driven piston. A hydraulic fluid of a fixed quantity fills the cavity between the drive piston and the driven piston to establish a hydraulic connection between the drive piston and the driven piston. The drive mechanism is drivably connected to the drive piston. The drive mechanism is configured to move the drive piston in the proximal cylinder. The elongate biopsy member is connected to the driven piston.

The invention in another form is directed to a biopsy device that includes a chamber housing configured to define a proximal cylinder, a distal cylinder, and a transition chamber interposed between the proximal cylinder and the distal cylinder. The chamber housing has a longitudinal axis with the proximal cylinder being separated from the distal cylinder by the transition chamber along the longitudinal axis. The proximal cylinder has a first diameter, and the distal cylinder has a second diameter, with the first diameter being larger than the second diameter. A drive piston is located in the proximal cylinder. A drive source has a motor coupled to a mechanical drive train. The mechanical drive train is connected to the drive piston. The drive source is configured to move the drive piston in the proximal cylinder along the longitudinal axis. A driven piston is located in the distal cylinder. The driven piston is configured to move in the distal cylinder along the longitudinal axis. A cavity is defined in the chamber housing between the drive piston and the driven piston, with the cavity including the transition chamber. A hydraulic fluid of a fixed quantity fills the cavity between the drive piston and the driven piston. A cannula is connected to the driven piston.

The invention in another form is directed to a biopsy device that includes a chamber housing having a proximal chamber, a transition chamber, and a distal chamber that form a continuous passage in the chamber housing. The proximal chamber, the transition chamber, and the distal chamber are arranged along a longitudinal axis. The proximal chamber has a first cylindrical side wall that has a first proximal end and a first distal end. The transition chamber has a frustoconical side wall that has a base end and a narrowed end. The distal chamber has a second cylindrical side wall that has a second proximal end and a second distal end. The base end of the frustoconical side wall is joined to the first distal end of the first cylindrical side wall and the narrowed end of the frustoconical side wall is joined to the second proximal end of the second cylindrical side wall. A drive piston is located in the proximal chamber. A drive source is connected to the drive piston, and the drive source is configured to move the drive piston in the proximal chamber along the longitudinal axis. A driven piston is located in the distal chamber. The driven piston is configured to move in the distal chamber along the longitudinal axis. A cavity is defined in the chamber housing between the drive piston and the driven piston. A hydraulic fluid of a fixed quantity fills the cavity between the drive piston and the driven piston. An elongate biopsy member is connected to the driven piston.

An advantage of the present invention is that the hydraulic drive assembly, e.g., having the drive piston and driven piston arrangement, eliminates the need for a mechanism having propelling/retracting springs, as in a typical biopsy driver.

BRIEF DESCRIPTION OF DRAWINGS

The above-mentioned and other features and advantages of this invention, and the manner of attaining them, will become more apparent and the invention will be better understood by reference to the following description of an embodiment of the invention taken in conjunction with the accompanying drawings, wherein.

Corresponding reference characters indicate corresponding parts throughout the several views. The exemplifications set out herein illustrate at least one embodiment of the invention, and such exemplifications are not to be construed as limiting the scope of the invention in any manner.

DESCRIPTION OF EMBODIMENTS

Figure 1:
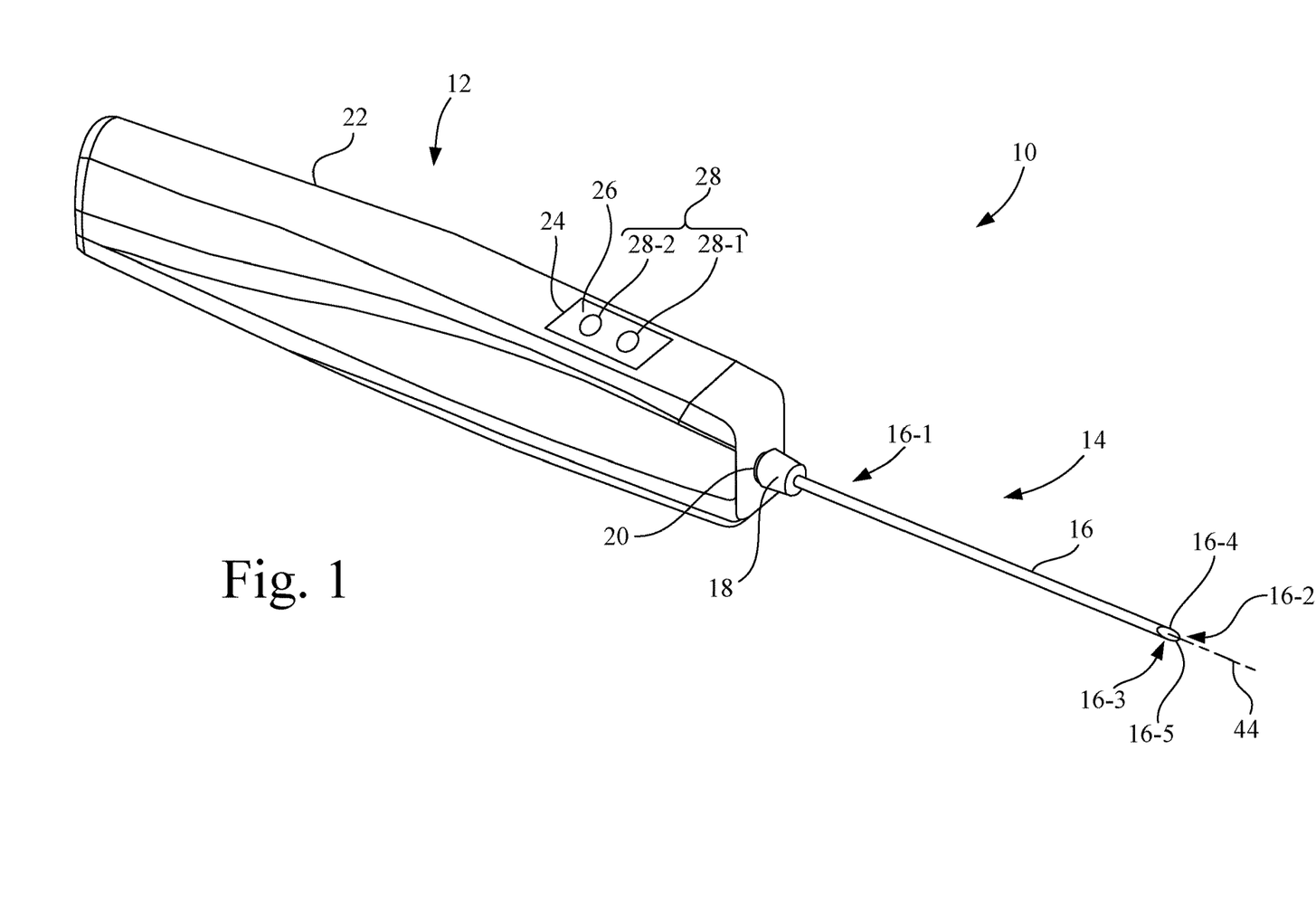
FIG. 1 is a perspective view of a biopsy device, configured in accordance with an embodiment of the present invention, with a disposable biopsy needle assembly mounted to a driver assembly.

Referring now to the drawings, and more particularly to FIG. 1, there is shown a biopsy device 10 which generally includes a driver assembly 12 and a disposable biopsy needle assembly 14. In the present embodiment, driver assembly 12 may be reusable on multiple patients, whereas disposable biopsy needle assembly 14 is used only on a single patient. Alternatively, driver assembly 12 also may be disposable. As used herein, the term "disposable" refers to a device that is intended for use with one patient only and is discarded after use.

Disposable biopsy needle assembly 14 includes an elongate biopsy member 16 and a connector 18. In the present embodiment, elongate biopsy member 16, such as a cannula, has a lumen 16-2, a beveled piercing tip portion 16-3 that defines an annular cutting edge 16-4, and a piercing tip 16-5. Those skilled in the art will recognize that elongate biopsy member 16 may have other tip configurations, such as blunted or forming a closed point, and may be used in conjunction with another coaxial cannula.

Connector 18 is fixedly attached to a proximal portion 16-1 of elongate biopsy member 16. Connector 18 is configured for releasable attachment to a needle mount interface 20 of driver assembly 12 (see also FIGS. 4-6). Connector 18 may be, for example, a screw-type connector, a bayonet mount, a snap-fit connector, or other suitable mechanism used to releasably connect two components.

Referring to FIG. 1, driver assembly 12 includes a handle housing 22. Handle housing 22 includes a window 24 for accessing a user interface circuit 26. User interface circuit 26 is configured to receive a user input and generate a user output signal. In the present embodiment, user interface circuit 26 may be a simple touch pad having a plurality of control buttons 28, individually identified as needle extend button 28-1 and needle retract button 28-2. Alternatively, it is contemplated that user interface circuit 26 may be a digital touch screen display.

Figure 2:
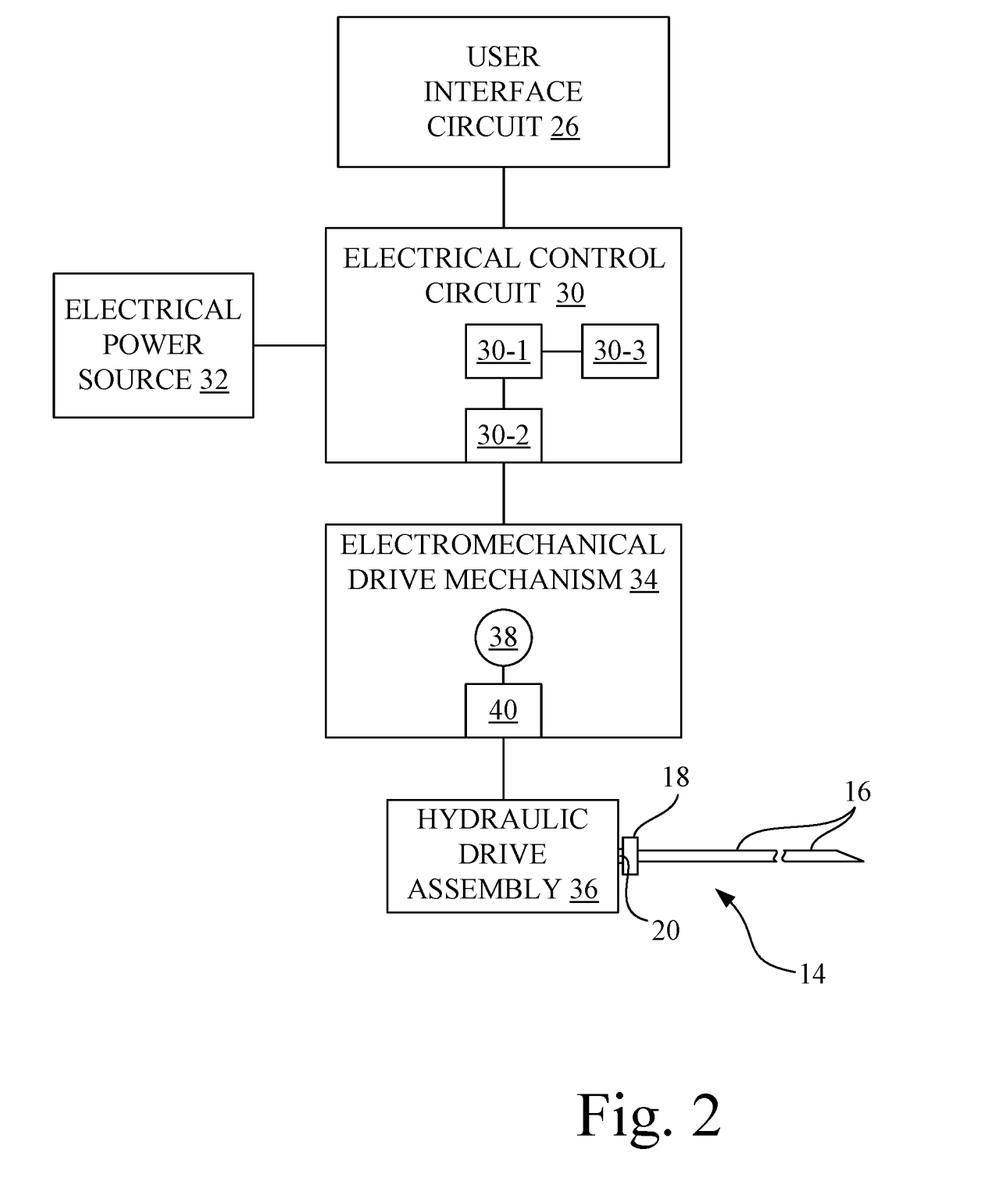
FIG. 2 is a block diagram depicting the user interface circuit, the electrical control circuit, the electrical power source, the electromechanical drive mechanism, the hydraulic drive assembly, and the disposable biopsy member of the biopsy device of FIG. 1.

Referring also to FIG. 2, handle housing 22 includes an interior open space to contain an electrical control circuit 30, an electrical power source 32, an electromechanical drive mechanism 34, and a hydraulic drive assembly 36. Electrical control circuit 30 is electrically coupled to electrical power source 32 to receive electrical power therefrom. Electrical power source 32 may be, for example, a rechargeable battery sized to have electrical capacity sufficient to supply the electrical power requirements of electrical control circuit 30, user interface circuit 26, and electromechanical drive mechanism 34. Those skilled in the art will recognize that user interface circuit 26 may receive power via electrical control circuit 30, or alternatively, from electrical power source 32. Likewise, those skilled in the art will recognize that electromechanical drive mechanism 34 may receive power via electrical control circuit 30, or alternatively, from electrical power source 32.

Electrical control circuit 30 includes a microcontroller 30-1, a motor interface circuit 30-2, and a sensor circuit 30-3.

Microcontroller 30-1 includes a microprocessor, on-board non-transitory electronic memory, and component interface circuitry, as is known in the art. Microcontroller 30-1 is configured to execute program instructions to generate motor control signals to control the extension and retraction of disposable biopsy needle assembly 14, based on the user output signal received from user interface circuit 26.

Motor interface circuit 30-2 is communicatively coupled to microcontroller 30-1 to receive the motor control signals. Motor interface circuit 30-2 includes power interface circuitry to supply electrical power, which may be in the form of control signals, to electromechanical drive mechanism 34.

Sensor circuit 30-3 may include, for example, an optical sensor, Hall-effect sensor, etc. that supplies a sensor output signal to microcontroller 30-1. In particular, sensor circuit 30-3 is located to sense a movement of a moveable component of electromechanical drive mechanism 34, such as a rotation of a drive gear or driven gear, as will be described in further detail below, and in turn to supply the sensor output signal corresponding to the sensed movement of the movable component of electromechanical drive mechanism 34 to microcontroller 30-1.

Electromechanical drive mechanism 34 includes a motor 38 and a mechanical drive train 40. Mechanical drive train 40 is coupled to receive rotary power from motor 38. Motor 38 may be, for example, a stepper motor or a DC (direct current) motor. Motor 38 receives electrical power, which may be in the form of control signals, from motor interface circuit 30-2 of electrical control circuit 30, and in turn provides rotary power to electromechanical drive mechanism 34 (see also FIGS. 4-6), as directed by electrical control circuit 30. As will be further described below, electromechanical drive mechanism 34 is configured to convert the rotary power received from motor 38 into linear power, which is supplied to hydraulic drive assembly 36.

Figure 3:
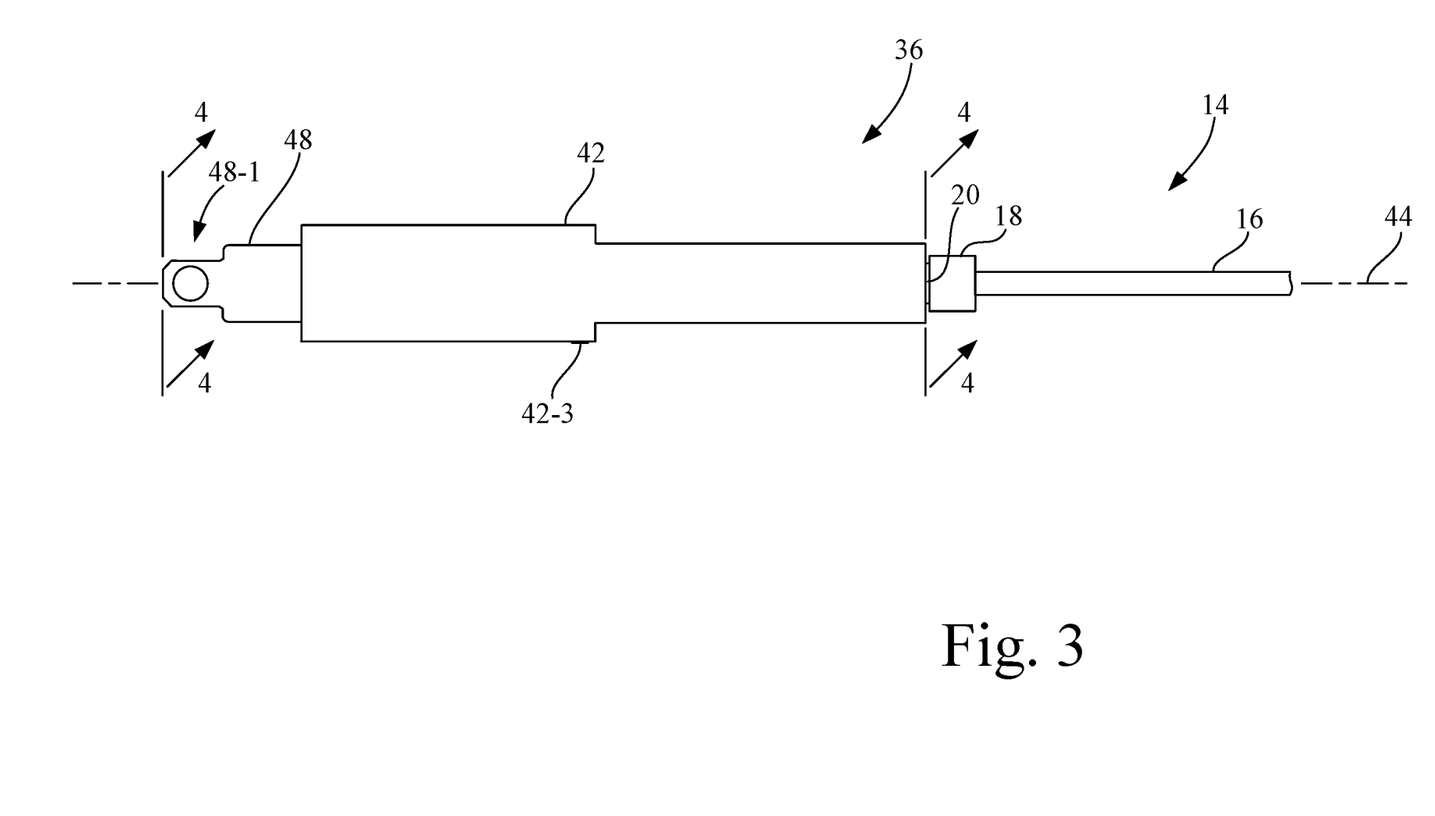
FIG. 3 is a side view of the hydraulic drive assembly of the biopsy device of FIG. 1.

FIG. 3 is a side view of hydraulic drive assembly 36, which is connected to disposable biopsy needle assembly 14. Hydraulic drive assembly 36 includes a chamber housing 42. Chamber housing 42 is arranged along a longitudinal axis 44.

Figure 4:
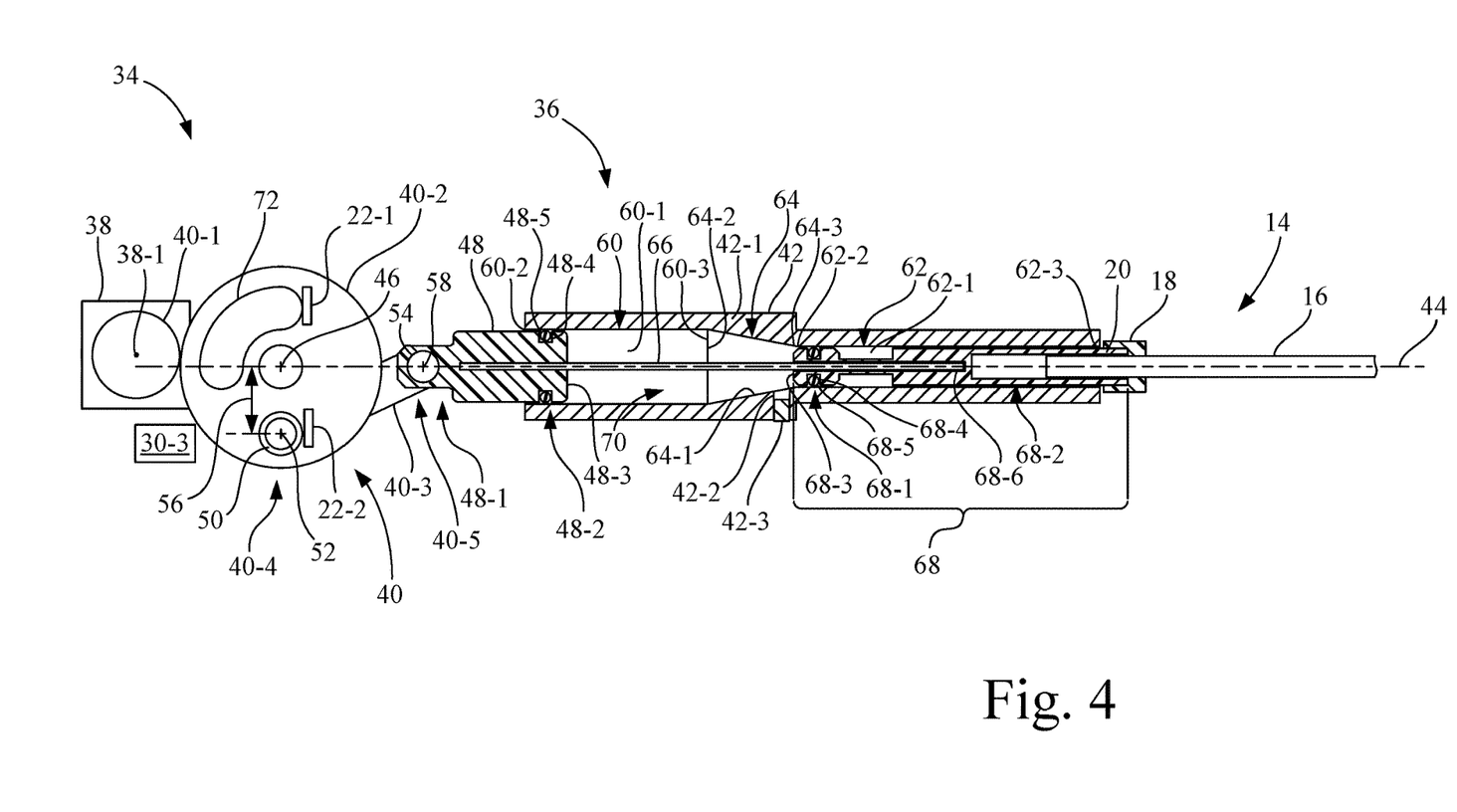
FIG. 4 is a section view of the hydraulic drive assembly of the biopsy device of FIG. 1, taken along plane 4-4 of FIG. 3, showing the electromechanical drive mechanism connected to the hydraulic drive assembly, and depicting a fully retracted position of the drive piston, the driven piston, and the disposable biopsy needle assembly.
Figure 5:
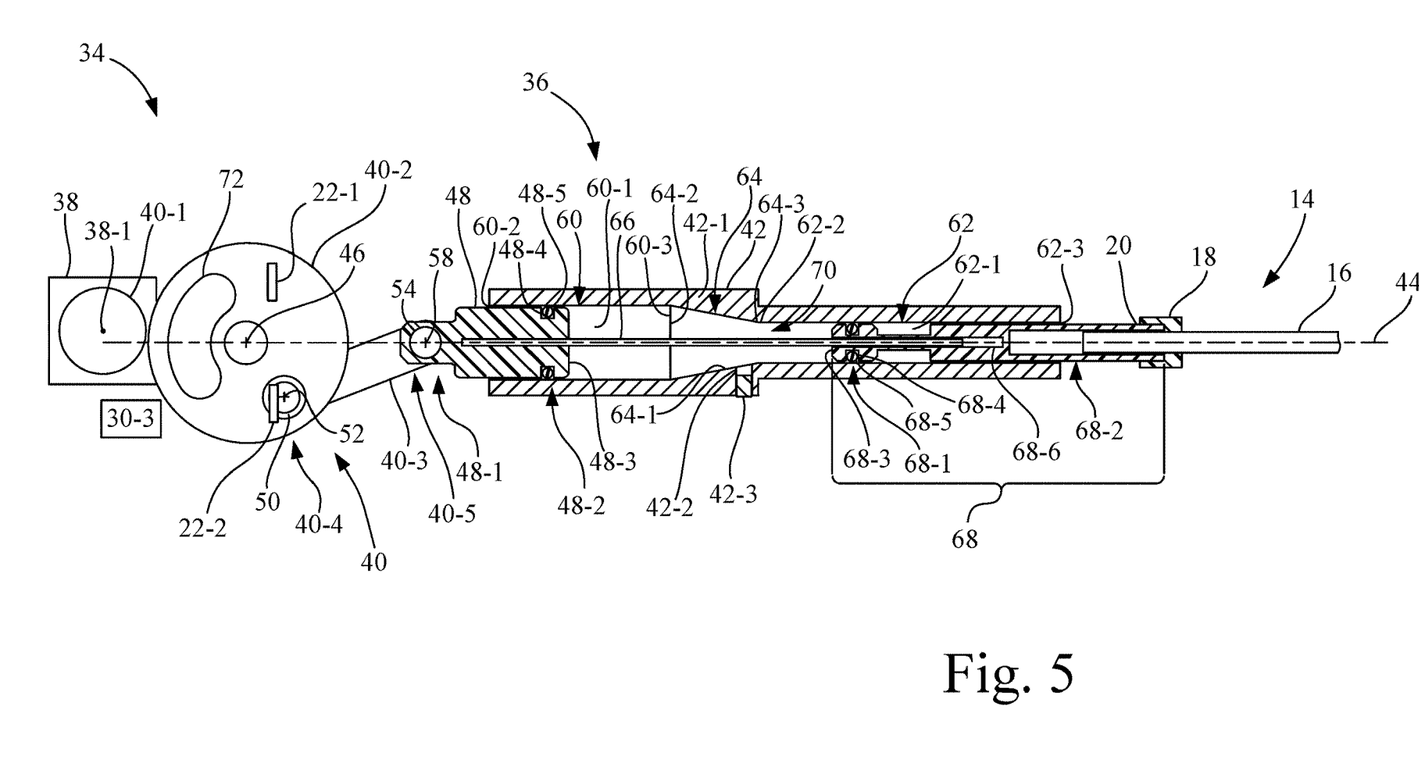
FIG. 5 is a section view of the hydraulic drive assembly of the biopsy device of FIG. 1, generally corresponding to FIG. 4, and depicting an intermediate position of the drive piston, the driven piston, and the disposable biopsy needle assembly.
Figure 6:
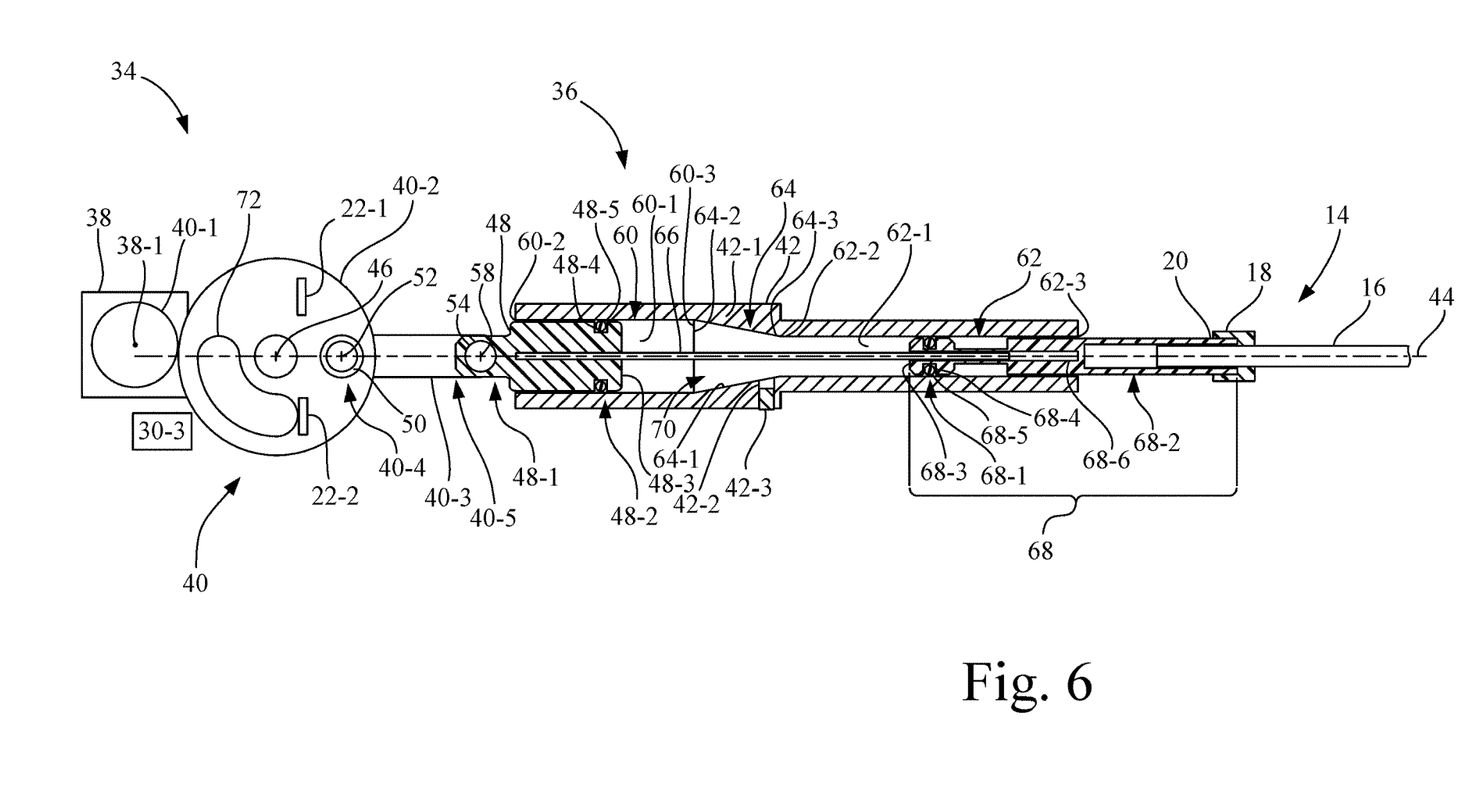
FIG. 6 is a section view of the hydraulic drive assembly of the biopsy device of FIG. 1, generally corresponding to FIG. 4, and depicting a fully extended position of the drive piston, the driven piston, and the disposable biopsy needle assembly.

Each of FIGS. 4-6 shows a side view of the electromechanical drive mechanism 34 and the hydraulic drive assembly 36, with hydraulic drive assembly 36 shown in cross-section along line 4-4 of FIG. 3. Electromechanical drive mechanism 34, serving as a drive source, is connected to hydraulic drive assembly 36.

Electromechanical drive mechanism 34 includes motor 38 and mechanical drive train 40. Motor 38 has a rotatable shaft 38-1. Mechanical drive train 40 includes a drive gear 40-1, a driven gear 40-2, and a drive link member 40-3. Drive gear 40-1 is fixedly attached to rotatable shaft 38-1 of motor 38, such that drive gear 40-1 rotates in unison with the rotation of rotatable shaft 38-1. Driven gear 40-2 is engaged, i.e., in mesh, with drive gear 40-1. Driven gear 40-2 is configured for mounting to handle housing 22, e.g., through bearing coupling to handle housing 22, and is located to rotate about a first rotational axis 46. The first rotational axis 46 of driven gear 40-2 is oriented to be substantially orthogonal to longitudinal axis 44, and in the present embodiment may further be oriented such that longitudinal axis 44 intersects first rotational axis 46. As used herein, the term "substantially orthogonal" equates to substantially perpendicular, and is defined to mean an angular relationship between two elements of 90 degrees, plus or minus 10 degrees.

Drive link member 40-3 may be configured as an elongate plate or rod, to facilitate a mechanical coupling of the driven gear to a movable drive component, e.g., a drive piston 48, of hydraulic drive assembly 36. Drive piston 48 has a first proximal end portion 48-1 and a first distal end portion 48-2. Drive link member 40-3 has a first end portion 40-4 and a second end portion 40-5 spaced apart from the first end portion 40-4.

A first connector 50 connects the first end portion 40-4 of drive link member 40-3 to driven gear 40-2. First connector 50 defines a second rotational axis 52 on driven gear 40-2 that is radially offset by an offset distance 56 from the first rotational axis 46. First connector 50 may be, for example, a pin/hole arrangement, wherein the first end portion 40-4 of drive link member 40-3 is rotatable about the second rotational axis 52 when a driving force is supplied by driven gear 40-2 to the first end portion 40-4 of drive link member 40-3 via first connector 50.

A second connector 54 connects the second end portion 40-5 of drive link member 40-3 to the movable drive component, e.g., drive piston 48, of hydraulic drive assembly 36. In the present embodiment, second connector 54 connects the second end portion 40-5 of drive link member 40-3 to the first proximal end portion 48-1 of drive piston 48. Second connector 54 defines a pivot axis 58 at the first proximal end portion 48-1 of drive piston 48. The pivot axis 58 is oriented to be substantially orthogonal to the longitudinal axis 44, and in the present embodiment may further be oriented such that longitudinal axis 44 intersects the pivot axis 58. Second connector 54 may be, for example, a pin/hole arrangement, wherein the second end portion 40-5 of drive link member 40-3 is pivotable about the pivot axis 58 when the driving force is transferred by drive link member 40-3 to the first proximal end portion 48-1 of drive piston 48, via second connector 54.

Hydraulic drive assembly 36 includes chamber housing 42 having a side wall 42-1 that is configured to define a proximal chamber 60, a distal chamber 62, and a transition chamber 64. Chamber housing 42 includes a hydraulic fluid fill passage 42-2 in the form of a cylindrical bore that extends through side wall 42-1. A removable fill plug 42-3 is sealably received in hydraulic fluid fill passage 42-2 of chamber housing 42, e.g., by press fit, or by a threaded connection between removable fill plug 42-3 and hydraulic fluid fill passage 42-2, with sealing tape or a seal coating applied to the threads.

Chamber housing 42 is positioned on longitudinal axis 44, with the proximal chamber 60 being separated from the distal chamber 62 by transition chamber 64 along longitudinal axis 44. In other words, transition chamber 64 is interposed between the proximal chamber 60 and the distal chamber 62. Proximal chamber 60, transition chamber 64, and distal chamber 62 form, collectively, a continuous passage in chamber housing 42 along longitudinal axis 44, with the continuous passage extending between the opposite end surfaces of chamber housing 42 along longitudinal axis 44.

Proximal chamber 60 has a first cylindrical side wall 60-1 having a first proximal end 60-2 and a first distal end 60-3, thereby defining a proximal cylinder. Distal chamber 62 has a second cylindrical side wall 62-1 having a second proximal end 62-2 and a second distal end 62-3, thereby defining a distal cylinder. Transition chamber 64 has a frustoconical side wall 64-1 having a base end 64-2 and a narrowed end 64-3. The base end 64-2 of the frustoconical side wall 64-1 is joined to the first distal end 60-3 of the first cylindrical side wall 60-1 of proximal chamber 60, and the narrowed end 64-3 of frustoconical side wall 64-1 is joined to the second proximal end 62-2 of the second cylindrical side wall 62-1 of distal chamber 62. First cylindrical side wall 60-1, frustoconical side wall 64-1, and second cylindrical side wall 62-1 may be formed as a continuous interior surface of chamber housing 42.

Drive piston 48 is located in the proximal chamber 60, with the first proximal end portion 48-1 of drive piston 48 extending in a proximal direction from chamber housing 42, and with at least first distal end portion 48-2 of drive piston 48 movably residing in proximal chamber 60. The first distal end portion 48-2 of drive piston 48 has a piston head 48-3 and an annular slot 48-4 that receives a seal member 48-5, such as a rubber O-ring, that annularly engages first cylindrical side wall 60-1 of proximal chamber 60.

The first proximal end portion 48-1 of drive piston 48 is connected to the second end portion 40-5 of drive link member 40-3 of mechanical drive train 40 of electromechanical drive mechanism 34, via first connector 50. Electromechanical drive mechanism 34, as controlled by electrical control circuit 30, is configured to move, i.e., linearly displace, the drive piston 48 in proximal chamber 60 along the longitudinal axis 44.

An optional guide rod 66 may be fixedly attached to drive piston 48, e.g., by being press fit into a hole in drive piston 48. Guide rod 66 extends distally from piston head 48-3 along longitudinal axis 44.

A driven piston 68 is located in distal chamber 62. Driven piston 68 is configured to move in distal chamber 62 along the longitudinal axis 44. Driven piston 68 has a second proximal end portion 68-1 and a second distal end portion 68-2. The second proximal end portion 68-1 of the driven piston 68 has a piston tail 68-3 that is in an opposed relationship with piston head 48-3 of drive piston 48, with piston tail 68-3 of driven piston 68 being linearly spaced from piston head 48-3 of drive piston 48. The second proximal end portion 68-1 further has an annular slot 68-4 that receives a seal member 68-5, such as a rubber O-ring, which annularly engages second cylindrical side wall 62-1 of distal chamber 62.

The second distal end portion 68-2 of driven piston 68 includes the needle mount interface 20 that is configured to releasably connect to elongate biopsy member 16 of disposable biopsy needle assembly 14 via connector 18. Elongate biopsy member 16 is configured to longitudinally extend in a distal direction from needle mount interface 20 along longitudinal axis 44.

In an embodiment that includes guide rod 66, driven piston 68 includes a guide rod channel 68-6 sized to slidably receive the guide rod 66 that is fixedly attached to drive piston 48. As such, guide rod 66 may assist in maintaining an axial alignment of drive piston 48 and driven piston 68, without any sort of mechanical connection between drive piston 48 and driven piston 68 along longitudinal axis 44. In addition, guide rod 66 is useful in obtaining component alignment during assembly of hydraulic drive assembly 36.

Prior to filling hydraulic drive assembly 36 with hydraulic fluid, a cavity 70 is defined in chamber housing 42 between drive piston 48 and driven piston 68, with cavity 70 including transition chamber 64. The hydraulic fluid may be, for example, propylene glycol, or a silicone oil based fluid. Hydraulic fluid of a fixed quantity is received through hydraulic fluid fill passage 42-2, so as to fill cavity 70 between drive piston 48 and driven piston 68. As used herein, to "fill" cavity 70 means to completely occupy the space, i.e., volume, defined by cavity 70. In the present embodiment, hydraulic fluid will completely occupy the space defined by cavity 70, such that all air is removed from cavity 70. In other words, hydraulic fluid is received between drive piston 48 and driven piston 68, with each of piston head 48-3 of drive piston 48 and piston tail 68-3 of driven piston 68 facing the hydraulic fluid. With all air removed from cavity 70 in chamber housing 42, fill plug 42-3 is installed to seal cavity 70.

Thus, while there is no mechanical connection between drive piston 48 and driven piston 68, there is now a hydraulic connection between drive piston 48 and driven piston 68, such that a displacement of drive piston 48 along longitudinal axis 44 will result in an amplified displacement of driven piston 68 along longitudinal axis 44, by virtue of the configuration of the proximal chamber 60, transition chamber 64 and distal chamber 62. In other words, driven piston 68 and disposable biopsy needle assembly 14 will be driven at a faster linear speed than the linear speed of drive piston 48. Also, since hydraulic drive assembly 36 is a closed hydraulic system, the instant that motor 38 stops rotation of drive gear 40-1, the linear displacement of elongate biopsy member 16 of disposable biopsy needle assembly 14 will stop.

In the present embodiment, proximal chamber 60 may be a cylinder having a first diameter and distal chamber 62 may be a cylinder having a second diameter, wherein the first diameter is larger than the second diameter, and wherein each of the first diameter and the second diameter is transverse, i.e., orthogonal, to the longitudinal axis 44. The first diameter of the cylindrical proximal chamber 60 is associated with a corresponding first transverse area within proximal chamber 60, and the second diameter of the cylindrical distal chamber 62 is associated with a corresponding second transverse area within distal chamber 62. In one implementation of the present embodiment, for example, the first diameter of proximal chamber 60 is 10 millimeters (mm) and the second diameter of the distal chamber is 6 mm, which yields a length displacement of driven piston 68 that is 2.8 times the displacement of drive piston 48 along longitudinal axis 44.

It is also contemplated that at least one of proximal chamber 60 and distal chamber 62 may be non-cylindrical, e.g., elliptical, in a direction transverse to the direction of piston travel, in which case the relationship between the transverse sizes of proximal chamber 60 and distal chamber 62 may be better characterized in terms of a respective transverse area that is orthogonal to an axis of the respective chamber, e.g., the transverse area being orthogonal to the direction of piston travel. In the present example, proximal chamber 60 has a first transverse area orthogonal to longitudinal axis 44 and distal chamber 62 has a second transverse area orthogonal to longitudinal axis 44, wherein the direction of piston travel of both drive piston 48 and driven piston 68 is coincident with longitudinal axis 44, and wherein the first transverse area is larger than the second transverse area.

In operation, referring again to FIG. 1, user interface circuit 26 includes control buttons 28 that receive a user input, and it in turn generates a corresponding user output signal. In the present embodiment, sensor circuit 30-3 is configured and positioned to sense a rotation of driven gear 40-2 and generate a sensor output signal corresponding to the rotation of driven gear 40-2. Microcontroller 30-1 is in electrical communication with each of user interface circuit 26 and sensor circuit 30-3, and executes program instructions to process each of the user output signal and the sensor output signal, and to supply a motor control signal to motor interface circuit 30-2 to control operation of motor 38 in accordance with whether needle extend button 28-1 or needle retract button 28-2 is depressed.

In the orientation shown in FIGS. 4-6, depressing needle extend button 28-1 generates a user output signal that initiates a clockwise rotation of drive gear 40-1, which in turn results in a counterclockwise rotation of driven gear 40-2 and a linear displacement of drive piston 48 in the sequence depicted in FIGS. 4-6, wherein FIG. 4 depicts a fully retracted position of drive piston 48, driven piston 68, and disposable biopsy needle assembly 14; FIG. 5 depicts an intermediate position of drive piston 48, driven piston 68, and disposable biopsy needle assembly 14; and FIG. 6 depicts a fully extended position of drive piston 48, driven piston 68, and disposable biopsy needle assembly 14.

Accordingly, as depicted in FIGS. 4-6, a full extension of disposable biopsy needle assembly 14 is achieved by a one-quarter rotation of driven gear 40-2. Sensor circuit 30-3 supplies a sensor output signal to microcontroller 30-1, which in turn processes the sensor output signal to maintain a range of motion driven gear 40-2 in the one-quarter rotation range depicted in FIGS. 4 and 6. In other words, the sensor output signal of sensor circuit 30-3 facilitates a stopping of the rotation of driven gear 40-2 after driven gear 40-2 has displaced drive piston 48 by a first linear distance, as determined by monitoring the rotation of driven gear 40-2. The displacement of drive piston 48 by the first linear distance results in a displacement of the driven piston 68 by a second linear distance, with the second linear distance being greater than the first linear distance. In turn, the displacement of driven piston 68 by the second linear distance also displaces elongate biopsy member 16 of disposable biopsy needle assembly 14 by the second linear distance.

Alternatively, or in addition, to the use of sensor circuit 30-3 in controlling the range of rotation of driven gear 40-2, mechanical stops 22-1 and 22-2, having respective stop surfaces, may be provided in the interior of handle housing 22, so as to be engaged by a protrusion 72, e.g., a rubber bumper, that extends from the side of driven gear 40-2, wherein mechanical stops 22-1 and 22-2 are positioned to define a physical limit to the amount of rotation that driven gear 40-2 is permitted to rotate. At least one mechanical stop may be used to limit a rotation of driven gear 40-2 to a rotational range of less than 360 degrees, and in the present option, two mechanical stops 22-1 and 22-2 are used to physically limit the rotation of driven gear 40-2, e.g., to a range of one-quarter rotation.

In the embodiments described above, hydraulic drive assembly 36 is implemented as a permanent component of driver assembly 12. However, as an alternative implementation of the present invention, it is contemplated that hydraulic drive assembly 36 may itself be disposable, and/or may be incorporated into disposable biopsy needle assembly 14.

The following items also relate to the invention:

In one form, the invention relates to a biopsy device having a hydraulic drive assembly, a drive mechanism, and an elongate biopsy member.

The hydraulic drive assembly includes a chamber housing configured to define a proximal chamber, a distal chamber, and a transition chamber. The transition chamber is interposed between the proximal chamber and the distal chamber, wherein the proximal chamber, the transition chamber, and the distal chamber collectively form a continuous passage in the chamber housing. The proximal chamber has a first transverse area and the distal chamber has a second transverse area, with the first transverse area being larger than the second transverse area. A drive piston is located in the proximal chamber and is configured to move in the proximal chamber. A driven piston is located in the distal chamber and is configured to move in the distal chamber. A cavity is defined in the chamber housing between the drive piston and the driven piston. A hydraulic fluid of a fixed quantity fills the cavity between the drive piston and the driven piston to establish a hydraulic connection between the drive piston and the driven piston.

The drive mechanism is drivably connected to the drive piston. The drive mechanism is configured to move the drive piston in the proximal cylinder. The elongate biopsy member is connected to the driven piston.

Optionally, the drive piston has a first proximal end portion and a first distal end portion. The first distal end portion of the drive piston may have a piston head that faces the hydraulic fluid. The drive mechanism may include a motor, a drive gear, a driven gear and a drive link member. The motor may have a rotatable shaft, and the drive gear may be attached to the rotatable shaft. The driven gear may be engaged with the drive gear. The driven gear may be configured to rotate about a first rotational axis. The drive link member may be configured to couple the driven gear to the first proximal end portion of the drive piston.

The drive link member may have a first end portion and a second end portion spaced apart from the first end portion. The first end portion of the drive link member may be rotatably coupled to the driven gear at a second rotational axis radially offset by an offset distance from the first rotational axis. The second end portion of the drive link member may be rotatably coupled to the first proximal end portion of the drive piston at a pivot axis at the first proximal end portion of the drive piston.

In any of the embodiments, the chamber housing may have a longitudinal axis, with each of the proximal chamber, transition chamber, and distal chamber being arranged along the longitudinal axis. The pivot axis may be oriented to be substantially orthogonal to the longitudinal axis, and the longitudinal axis may intersect the pivot axis.

The biopsy device may further include a handle housing configured to contain the chamber housing and the drive mechanism. The driven piston may have a second proximal end portion and a second distal end portion. The second proximal end portion of the driven piston may have a piston tail that faces the hydraulic fluid in an opposed relationship with the piston head of the drive piston. The second distal end portion of the driven piston may include a needle mount interface configured to releasably connect to the elongate biopsy member, and the elongate biopsy member may be configured to extend from the needle mount interface.

The driven gear may include a mechanical stop that extends from a side surface of the driven gear. The mechanical stop may be configured to engage a stop surface in the handle housing to limit a rotation of the driven gear to a rotational range of less than 360 degrees.

The biopsy device may further include a user interface circuit configured to receive a user input and generate a user output signal. A sensor circuit may be configured to sense a rotation of the driven gear and generate a sensor output signal. A motor interface circuit may be configured to supply electrical power to the motor. A microcontroller may be in electrical communication with each of the user interface circuit, the sensor circuit, and the motor interface circuit. The microcontroller may be configured to execute program instructions to process each of the user output signal and the sensor output signal, and to supply a motor control signal to the motor interface circuit to control operation of the motor.

The user interface circuit may be configured such that the user output signal initiates a rotation of the driven gear and the sensor output signal facilitates a stopping of the rotation of the driven gear after the driven gear has displaced the drive piston by a first linear distance.

The user interface circuit may be configured such that the displacement of the drive piston by the first linear distance results in a displacement of the driven piston by a second linear distance. The second linear distance may be greater than the first linear distance.

The transition chamber may have a frustoconical side wall having a base end and a narrowed end, wherein the base end is joined to the proximal chamber and the narrowed end is joined to the distal chamber.

For example, the proximal chamber may have a first cylindrical side wall having a first proximal end and a first distal end. The transition chamber may have a frustoconical side wall having a base end and a narrowed end. The distal chamber may have a second cylindrical side wall having a second proximal end and a second distal end. The base end of the frustoconical side wall is joined to the first distal end of the first cylindrical side wall and the narrowed end of the frustoconical side wall is joined to the second proximal end of the second cylindrical side wall.

In any of the biopsy devices described above, the proximal chamber may be a cylinder having a first diameter and the distal chamber may be a cylinder having a second diameter, wherein the first diameter is larger than the second diameter.

In another form, the invention relates to a biopsy device having a chamber housing configured to define a proximal cylinder, a distal cylinder, and a transition chamber interposed between the proximal cylinder and the distal cylinder. The chamber housing may have a longitudinal axis. The proximal cylinder is separated from the distal cylinder by the transition chamber along the longitudinal axis. The proximal cylinder has a first diameter and the distal cylinder has a second diameter, with the first diameter being larger than the second diameter. A drive piston is located in the proximal cylinder. A drive source may have a motor coupled to a mechanical drive train, with the mechanical drive train being connected to the drive piston. The drive source is configured to move the drive piston in the proximal cylinder along the longitudinal axis. A driven piston is located in the distal cylinder. The driven piston is configured to move in the distal cylinder along the longitudinal axis. A cavity is defined in the chamber housing between the drive piston and the driven piston. The cavity may include the transition chamber. A hydraulic fluid of a fixed quantity fills the cavity between the drive piston and the driven piston. A cannula is connected to the driven piston.

The drive source may include a motor, a drive gear, a driven gear, and a drive link member. The motor may have a rotatable shaft. The drive gear is attached to the rotatable shaft. The driven gear is engaged with the drive gear. The driven gear is configured to rotate about a first rotational axis. The first rotational axis of the driven gear may be oriented to be substantially orthogonal to the longitudinal axis. The longitudinal axis may intersect the rotational axis. The drive link member is configured to couple the driven gear to the drive piston.

The drive link member may have a first end portion and a second end portion. The drive piston may have a piston head and a piston tail that is linearly spaced from the piston head. A first connector may connect the first end portion of the drive link member to the driven gear. The first connector may define a second rotational axis on the driven gear that is radially offset by an offset distance from the first rotational axis. A second connector may connect the second end portion of the drive link member to the piston tail of the drive piston. The second connector may define a pivot axis at the piston tail of the drive piston.

The pivot axis may be oriented to be substantially orthogonal to the longitudinal axis. The longitudinal axis may intersect the pivot axis.

The biopsy device may further include a user interface circuit configured to receive a user input and generate a user output signal. A sensor circuit may be configured to sense a rotation of the driven gear and generate a sensor output signal. A motor interface circuit may be configured to supply electrical power to the motor. A microcontroller may be in electrical communication with each of the user interface circuit, the sensor circuit, and the motor interface circuit. The microcontroller may be configured to execute program instructions to process each of the user output signal and the sensor output signal and to supply a motor control signal to the motor interface circuit to control operation of the motor.

The user interface circuit may be configured such that the user output signal may initiate a rotation of the driven gear and the sensor output signal may facilitate a stopping of the rotation of the driven gear after the driven gear has displaced the drive piston by a first linear distance.

The user interface circuit may be configured such that the displacement of the drive piston by the first linear distance results in a displacement of the driven piston by a second linear distance. The second linear distance may be greater than the first linear distance.

The transition chamber may have a frustoconical side wall having a base end and a narrowed end, with the base end being joined to the proximal cylinder and the narrowed end being joined to the distal cylinder.

The driven piston may include a needle mount interface configured to releasably connect to the cannula.

In another form, the invention relates to a biopsy device including a chamber housing having a proximal chamber, a transition chamber, and a distal chamber that form a continuous passage in the chamber housing. The chamber housing may have a longitudinal axis along which the proximal chamber, the transition chamber, and the distal chamber are arranged. The proximal chamber has a first cylindrical side wall that has a first proximal end and a first distal end. The transition chamber may have a frustoconical side wall that has a base end and a narrowed end. The distal chamber may have a second cylindrical side wall that has a second proximal end and a second distal end. The base end of the frustoconical side wall is joined to the first distal end of the first cylindrical side wall and the narrowed end of the frustoconical side wall is joined to the second proximal end of the second cylindrical side wall. A drive piston is located in the proximal chamber. A drive source is connected to the drive piston. The drive source is configured to move the drive piston in the proximal chamber along the longitudinal axis. A driven piston is located in the distal chamber, the driven piston configured to move in the distal chamber along the longitudinal axis. A cavity is defined in the chamber housing between the drive piston and the driven piston. A hydraulic fluid of a fixed quantity fills the cavity between the drive piston and the driven piston. An elongate biopsy member is connected to the driven piston.

The drive piston may have a first proximal end portion and a first distal end portion. The first distal end portion of the drive piston may have a piston head that faces the hydraulic fluid.

The drive source may include a motor having a rotatable shaft. A drive gear is attached to the rotatable shaft. A driven gear may be engaged with the drive gear. The driven gear is configured to rotate about a first rotational axis. The first rotational axis of the driven gear may be oriented to be substantially orthogonal to the longitudinal axis. The longitudinal axis may intersect the first rotational axis. A drive link member may be configured to couple the driven gear to the first proximal end portion of the drive piston.

The drive link member has a first end portion and a second end portion spaced apart from the first end portion. The first end portion of the drive link member may be rotatably coupled to the driven gear at a second rotational axis radially offset by an offset distance from the first rotational axis. The second end portion of the drive link member may be rotatably coupled to the first proximal end portion of the drive piston at a pivot axis at the first proximal end portion of the drive piston. The pivot axis may be oriented to be substantially orthogonal to the longitudinal axis. The longitudinal axis may intersect the pivot axis.

In any of the embodiments, the biopsy device may further include a handle housing configured to contain the chamber housing and the drive source, and wherein the driven piston may have a second proximal end portion and a second distal end portion. The second proximal end portion of the driven piston may have a piston tail that faces the hydraulic fluid in an opposed relationship with the piston head of the drive piston. The second distal end portion of the driven piston may include a needle mount interface configured to releasably connect to the elongate biopsy member. The elongate biopsy member is configured to longitudinally extend from the needle mount interface.

The driven gear may include a mechanical stop that extends from a side surface of the driven gear. The mechanical stop may be configured to engage a stop surface in the handle housing to limit a rotation of the driven gear to a rotational range of less than 360 degrees.

The biopsy device may further includes a user interface circuit configured to receive a user input and generate a user output signal. A sensor circuit may be configured to sense a rotation of the driven gear and generate a sensor output signal. A motor interface circuit may be configured to supply electrical power to the motor. A microcontroller may be in electrical communication with each of the user interface circuit, the sensor circuit, and the motor interface circuit. The microcontroller may be configured to execute program instructions to process each of the user output signal and the sensor output signal, and to supply a motor control signal to the motor interface circuit to control operation of the motor.

The user interface circuit may be configured such that the user output signal may initiate a rotation of the driven gear and the sensor output signal may facilitate a stopping of the rotation of the driven gear after the driven gear has displaced the drive piston by a first linear distance.

The user interface circuit may be configured such that the displacement of the drive piston by the first linear distance results in a displacement of the driven piston by a second linear distance. The second linear distance may be greater than the first linear distance.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A biopsy device, comprising:
   a hydraulic drive assembly that includes:
      a chamber housing configured to define a proximal chamber, a distal chamber, and a transition chamber, the transition chamber being interposed between the proximal chamber and the distal chamber, wherein the proximal chamber, the transition chamber, and the distal chamber collectively form a continuous passage in the chamber housing, the proximal chamber having a first transverse area and the distal chamber having a second transverse area, the first transverse area being larger than the second transverse area;
      a drive piston located in the proximal chamber and configured to move in the proximal chamber;
      a driven piston located in the distal chamber and configured to move in the distal chamber;
      a cavity defined in the chamber housing between the drive piston and the driven piston; and
      a hydraulic fluid of a fixed quantity that fills the cavity between the drive piston and the driven piston to establish a hydraulic connection between the drive piston and the driven piston;
   a drive mechanism drivably connected to the drive piston, the drive mechanism configured to move the drive piston in the proximal cylinder; and
   an elongate biopsy member connected to the driven piston.

2. The biopsy device according to claim 1, wherein the drive piston has a first proximal end portion and a first distal end portion, the first distal end portion of the drive piston having a piston head that faces the hydraulic fluid, and the drive mechanism includes:
   a motor having a rotatable shaft;
   a drive gear attached to the rotatable shaft;
   a driven gear engaged with the drive gear, the driven gear configured to rotate about a first rotational axis; and
   a drive link member configured to couple the driven gear to the first proximal end portion of the drive piston.

3. The biopsy device according to claim 2, wherein the drive link member has a first end portion and a second end portion spaced apart from the first end portion, the first end portion of the drive link member being rotatably coupled to the driven gear at a second rotational axis radially offset by an offset distance from the first rotational axis, and the second end portion of the drive link member being rotatably coupled to the first proximal end portion of the drive piston at a pivot axis at the first proximal end portion of the drive piston.

4. The biopsy device according to claim 3, wherein the chamber housing has a longitudinal axis, with each of the proximal chamber, the transition chamber, and the distal chamber being arranged along the longitudinal axis, and the pivot axis is oriented to be substantially orthogonal to the longitudinal axis, the longitudinal axis intersecting the pivot axis.

5. The biopsy device according to claim 2, comprising a handle housing configured to contain the chamber housing and the drive mechanism, wherein the driven piston has a second proximal end portion and a second distal end portion, the second proximal end portion of the driven piston having a piston tail that faces the hydraulic fluid in an opposed relationship with the piston head of the drive piston, and wherein the second distal end portion of the driven piston includes a needle mount interface configured to releasably connect to the elongate biopsy member, the elongate biopsy member configured to extend from the needle mount interface.

6. The biopsy device according to claim 5, wherein the driven gear includes a mechanical stop that extends from a side surface of the driven gear, the mechanical stop configured to engage a stop surface in the handle housing to limit a rotation of the driven gear to a rotational range of less than 360 degrees.

7. The biopsy device according to claim 2, comprising:
   a user interface circuit configured to receive a user input and generate a user output signal;
   a sensor circuit configured to sense a rotation of the driven gear and generate a sensor output signal;
   a motor interface circuit configured to supply electrical power to the motor; and
   a microcontroller in electrical communication with each of the user interface circuit, the sensor circuit, and the motor interface circuit, the microcontroller configured to execute program instructions to process each of the user output signal and the sensor output signal, and to supply a motor control signal to the motor interface circuit to control operation of the motor.

8. The biopsy device according to claim 7, wherein the user output signal initiates a rotation of the driven gear and the sensor output signal facilitates a stopping of the rotation of the driven gear after the driven gear has displaced the drive piston by a first linear distance.

9. The biopsy device according to claim 8, wherein the displacement of the drive piston by the first linear distance results in a displacement of the driven piston by a second linear distance, the second linear distance being greater than the first linear distance.

10. The biopsy device according to claim 1, wherein the transition chamber has a frustoconical side wall having a base end and a narrowed end, the base end being joined to the proximal chamber and the narrowed end being joined to the distal chamber.

11. The biopsy device according to claim 1, wherein the proximal chamber has a first cylindrical side wall having a first proximal end and a first distal end, the transition chamber has a frustoconical side wall having a base end and a narrowed end, and the distal chamber has a second cylindrical side wall having a second proximal end and a second distal end, the base end of the frustoconical side wall being joined to the first distal end of the first cylindrical side wall and the narrowed end of the frustoconical side wall being joined to the second proximal end of the second cylindrical side wall.

12. The biopsy device according to claim 1, wherein the proximal chamber is a cylinder having a first diameter and the distal chamber is a cylinder having a second diameter, the first diameter being larger than the second diameter.

13. A biopsy device, comprising:
   a chamber housing configured to define a proximal cylinder, a distal cylinder, and a transition chamber interposed between the proximal cylinder and the distal cylinder, the chamber housing having a longitudinal axis and with the proximal cylinder being separated from the distal cylinder by the transition chamber along the longitudinal axis, the proximal cylinder having a first diameter and the distal cylinder having a second diameter, the first diameter being larger than the second diameter;
   a drive piston located in the proximal cylinder;
   a drive source having a motor coupled to a mechanical drive train, the mechanical drive train being connected to the drive piston, the drive source configured to move the drive piston in the proximal cylinder along the longitudinal axis;
   a driven piston located in the distal cylinder, the driven piston configured to move in the distal cylinder along the longitudinal axis;
   a cavity defined in the chamber housing between the drive piston and the driven piston, the cavity including the transition chamber;
   a hydraulic fluid of a fixed quantity that fills the cavity between the drive piston and the driven piston; and
   a cannula connected to the driven piston.

14. The biopsy device according to claim 13, the drive source comprising:
   a motor having a rotatable shaft;
   a drive gear attached to the rotatable shaft;
   a driven gear engaged with the drive gear, the driven gear configured to rotate about a first rotational axis, the first rotational axis of the driven gear being oriented to be substantially orthogonal to the longitudinal axis, the longitudinal axis intersecting the first rotational axis; and
   a drive link member configured to couple the driven gear to the drive piston.

15. The biopsy device according to claim 14, wherein the drive link member has a first end portion and a second end portion, and the drive piston has a piston head and a piston tail that is linearly spaced from the piston head;
   a first connector that connects the first end portion of the drive link member to the driven gear, the first connector defining a second rotational axis on the driven gear that is radially offset by an offset distance from the first rotational axis, and
   a second connector that connects the second end portion of the drive link member to the piston tail of the drive piston, the second connector defining a pivot axis at the piston tail of the drive piston.

16. The biopsy device according to claim 15, wherein the pivot axis is oriented to be substantially orthogonal to the longitudinal axis, the longitudinal axis intersecting the pivot axis.

17. The biopsy device according to claim 14, comprising:
   a user interface circuit configured to receive a user input and generate a user output signal;
   a sensor circuit configured to sense a rotation of the driven gear and generate a sensor output signal;
   a motor interface circuit configured to supply electrical power to the motor; and
   a microcontroller in electrical communication with each of the user interface circuit, the sensor circuit, and the motor interface circuit, the microcontroller configured to execute program instructions to process each of the user output signal and the sensor output signal and to supply a motor control signal to the motor interface circuit to control operation of the motor.

18. The biopsy device according to claim 17, wherein the user output signal initiates a rotation of the driven gear and the sensor output signal facilitates a stopping of the rotation of the driven gear after the driven gear has displaced the drive piston by a first linear distance.

19. The biopsy device according to claim 18, wherein the displacement of the drive piston by the first linear distance results in a displacement of the driven piston by a second linear distance, the second linear distance being greater than the first linear distance.

20. A biopsy device, comprising:
   a chamber housing configured to define a proximal cylinder, a distal cylinder, and a transition chamber interposed between the proximal cylinder and the distal cylinder, the chamber housing having a longitudinal axis and with the proximal cylinder being separated from the distal cylinder by the transition chamber along the longitudinal axis, the proximal cylinder having a first diameter and the distal cylinder having a second diameter, the first diameter being larger than the second diameter;
   a drive piston located in the proximal cylinder;
   a drive source having a motor coupled to a mechanical drive train, the mechanical drive train being connected to the drive piston, the drive source configured to move the drive piston in the proximal cylinder along the longitudinal axis;
   a driven piston located in the distal cylinder, the driven piston configured to move in the distal cylinder along the longitudinal axis;
   a cavity defined in the chamber housing between the drive piston and the driven piston, the cavity including the transition chamber;
   a hydraulic fluid of a fixed quantity that fills the cavity between the drive piston and the driven piston; and
   a cannula connected to the driven piston,
   wherein the transition chamber has a frustoconical side wall having a base end and a narrowed end, the base end being joined to the proximal cylinder and the narrowed end being joined to the distal cylinder.

21. The biopsy device according to claim 20, wherein the driven piston includes a needle mount interface configured to releasably connect to the cannula.

* * * * *